United States Patent [19]
Takehashi

[11] Patent Number: 5,274,865
[45] Date of Patent: Jan. 4, 1994

[54] COOLING DEVICE
[75] Inventor: Takeshige Takehashi, Toyama, Japan
[73] Assignee: Sanwa Life Cela Kabushiki Kaisha, Toyama, Japan
[21] Appl. No.: 981,787
[22] Filed: Nov. 25, 1992
[51] Int. Cl.⁵ .................. A61F 7/00; A47C 20/02
[52] U.S. Cl. .................................. 5/644; 5/421; 5/643; 62/530; 607/153; 607/109; 607/149
[58] Field of Search .............. 129/380, 384, 402, 403; 5/421, 643, 644; 62/530; 165/46

[56] References Cited
U.S. PATENT DOCUMENTS

| 1,488,743 | 4/1924 | Eggers | 128/402 |
|---|---|---|---|
| 3,075,529 | 1/1963 | Young, Jr. | 128/403 |
| 3,139,631 | 7/1964 | Kiefer | 5/643 |
| 3,780,537 | 12/1973 | Spencer | 62/530 |
| 4,676,247 | 6/1987 | Van Cleve | 128/403 X |
| 4,783,866 | 11/1988 | Simmons et al. | 5/421 X |
| 4,865,012 | 9/1989 | Kelley | 128/403 X |
| 4,887,326 | 12/1989 | O'Brien et al. | 5/421 |
| 4,910,978 | 3/1990 | Gordon et al. | 62/530 |
| 5,198,804 | 9/1992 | Hill et al. | 128/402 |

Primary Examiner—Michael F. Trettel
Attorney, Agent, or Firm—Flynn, Thiel, Boutell & Tanis

[57] ABSTRACT

One aspect of the invention is a cooling pillow comprising a flexible pouch and thermal transfer fluid composition hermetically filled in the pouch. A second aspect of the invention is a cooling device which comprises a pad having a flexible pouch and a thermal transfer fluid composition hermetically filled in the pouch, and means for holding the pad therewith to bring the pad in contact with the human body. The fluid composition comprises a mixture of fine particles of hard or graphitic carbon having good thermal conductivity and water. Sodium chloride, surface active agents, bactericides and preservatives may be further added to the composition. Since the carbon particles have good thermal conductivity, the fluid readily reaches a temperature close to ambient temperatures and can gently cool the human body. Long use allows the body to be continuously cooled down to a temperature close to the ambient temperature.

10 Claims, 3 Drawing Sheets

COOLING DEVICE

BACKGROUND OF THE INVENTION

1. Field of The Invention

This invention relates to a cooling device having a cooling substance contained in a pillow or holder which are used for direct contact with the human body.

2. Description of the Prior Art

There exist various types of pillows including a grass pillow, a wooden pillow, a stone pillow, a porcelain pillow, etc. which are used on beds. However, since these pillows feel hard to a user's head, there has been employed recently a stuffed pillow which fills various materials in a bag-shaped cloth and a flat pillow. The cloth used in the pillows is normally a cotton cloth and is filled with cotton, buckwheat hulls, adzuki beans, tea grounds and rice hulls.

The pillow has been variously designed to carry out a so-called "cooling head and heating leg" which is familiar as a key to health and long life. A water pillow is typical. There is a pillow having a body formed of a bundle of tubes through which air passes and a pillow having a plate body attached to the inside of the pillow in which the plate body is formed of a plurality of ceramic plates connected to one another in lengthwise and crosswise, etc.

In case of the water pillow, since it is filled with ice, the cooling effect relative to the head is very strong at the beginning which is used when the user injures his health and is feverish. However, it is not always useful for health care. Furthermore, ice should be refilled frequently since water radiates less heat when ice melts and the temperature of the pillow becomes gradually close to the body temperature and the cooling effect is lost at last.

Moreover, in the pillow having a bundle of tubes or the pillow having the plate body, a high keeping-cool property can not be attained although the heat exchange is effected due to air circulation or thermal transfer. Furthermore, these pillows can not be used comfortably since they feel hard to the user's head.

As a typical known holder for a cooling purpose, there is a type of band for cooling a head therewith, i.e. a so-called "Edison band". Nothing other than the cooling band is known as having been specifically developed. In order to mitigate a bruise or inflammation, it is usual to employ a sticking plaster which makes use of a poultice applied onto a pad cloth. For administration of first aid, cooling storage materials are held against the affected part through a towel or the like.

The head cooling band is made of a band tied around the head and a number of ceramic pieces attached to the band in a checkered pattern. The body heat is absorbed with the ceramic pieces, thereby cooling the head.

Since the known band tied around head has hard ceramic pieces, it is uncomfortable against the head. Especially, when one's head is sightly fastened with the band, pain is felt, making it impossible to use the band because it is comfortable.

The poultice plaster is applied by attachment to the affected part and is not uncomfortable. However, an odor of the ingredients contained in the poultice is relatively strong, inconveniently emanating the odor therearound. In addition, the ingredients sometimes stimulate the skin, causing a rash, an itch or an eruption to appear on or in the skin. On the other hand, cooling storage materials do not have a good thermal transfer rate and thus, the cooling time is long. However, once the stored cooling energy is lost, the cooling ability is lost completely with the problem that any further cooling effect cannot be expected.

SUMMARY OF THE INVENTION

It is accordingly an object of the invention to provide a cooling material contained in a pillow and a holder which overcomes the disadvantages of prior art counterparts.

It is another object of the invention to provide a cooling material contained in a pillow and a holder whose cooling effect can be long expected and whose temperature is invariably kept close to ambient temperatures whereby on contact with human body, the body can be comfortably cooled.

The above object can be achieved, according to the first aspect of the invention, by a cooling pillow which comprises a flexible pouch and a thermal transfer fluid hermetically filled in the flexible pouch wherein the thermal transfer fluid comprises a mixture of fine particles of hard carbon or graphitic carbon and water.

The above object can be achieved, according to the second aspect of the invention, by a cooling device which comprises a pad which has a flexible pouch and a thermal transfer fluid hermetically filled in the flexible pouch, and pad-holding means which keeps the pad in contact with a human body, the thermal transfer fluid comprising a mixture of fine particles of hard carbon or graphitic carbon and water.

Preferably, the fine particles have a size of 1 to 1000 μm, more preferably from 100 to 500 μm.

Moreover, it is preferred that the fluid should further comprise a surface active agent, sodium chloride and small amounts of bactericides and preservatives.

PREFERRED EMBODIMENTS OF THE INVENTION

Figure 1:
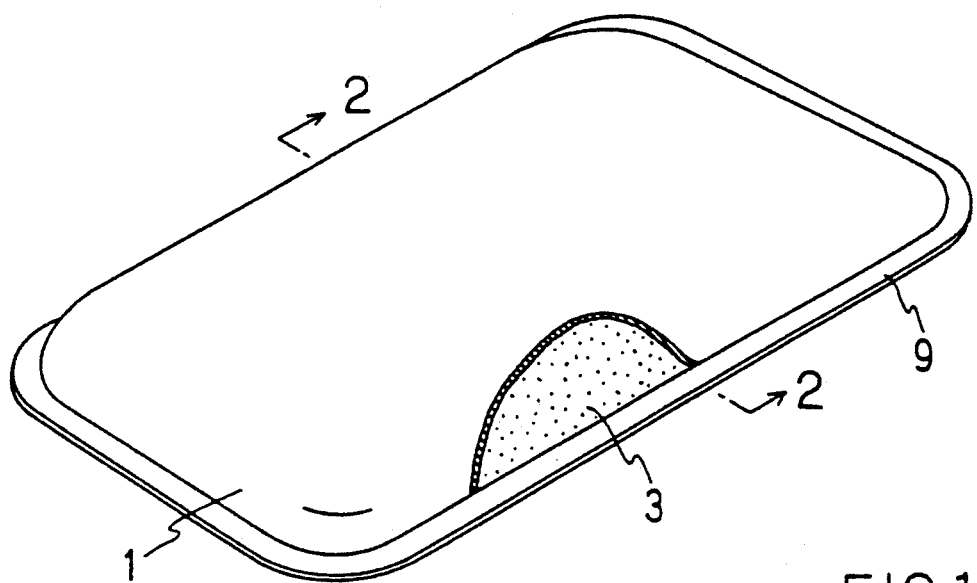
FIG. 1 is a perspective view of a cooling pillow according to a first embodiment of the present invention.
Figure 2:
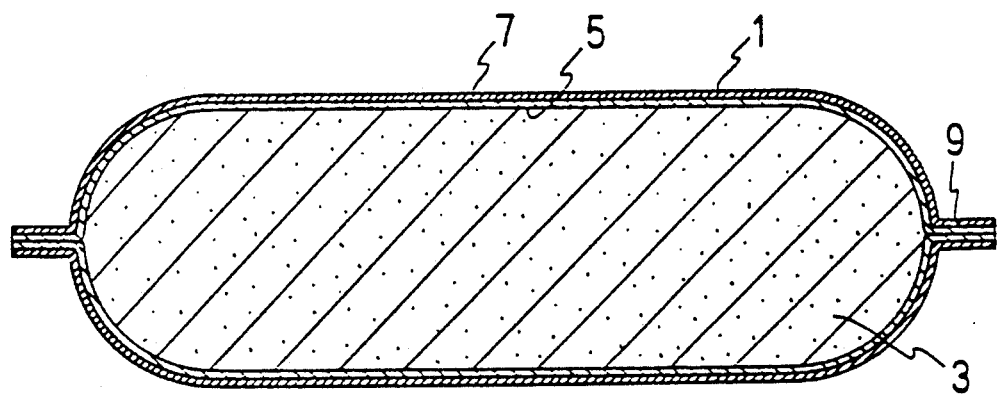
FIG. 2 is an enlarged sectional view of the pillow taken along the line A—A of FIG. 1.

First Embodiment (FIGS. 1 and 2)

A cooling device pillow according to a first embodiment will be described with reference to FIGS. 1 and 2.

The pillow comprises a flexible pouch 1 and a thermal transfer fluid 3 having an excellent thermal conductivity wherein the former is hermetically filled with the latter.

The flexible pouch 1 may be made of a flexible composite film, which includes a laminate of a nylon outer film 5 which feels good to the touch and a firm polyester inner film 7. The flexible pouch 1 is subjected to a heat fusing at the periphery whereby a heat fused flange edge 9 is provided at the periphery thereof. For hermetically sealing, the thermal transfer fluid 3 is filled up in the flexible pouch 1, followed by heat sealing under a vacuumizing condition. By this, the phase separation and spoilage of the thermal transfer fluid can be suppressed to a significant extent with an attendant advantage that the thermal conductivity can be enhanced owing to the degassing.

The thermal transfer fluid 3 comprises the following composition which are kneaded in a kneader for 20 to 30 minutes.

| Fixed carbon powder | 50 Kg |
|---|---|
| Water | 35 Kg |
| Glycerin | 2 Kg |
| Sodium chloride | 15 Kg |
| Sodium hypochlorite | 250 cc |
| Sodium dehydroacetate | 250 cc |

The thermal transfer fluid 3 should comprise fine particles of hard carbon or graphitic or fixed carbon dispersed in water. The fine particles of the carbon used in the present invention should preferably have a purity of 99.4% or over and a size of from 1 to 1000 micrometers. More preferably, the size is from 100 to 500 micrometers on average. The mixture should be fluid after mixing of the fine particles and water. Preferably, the mixing ratio between the fine particles and water is in the range of 75:25 to 60:40 on the weight basis, within which good fluidity and good thermal conductivity are ensured.

The fixed carbon particles may be obtained by molding a coke or pitch in the intended form and heating the resulting molded product to about 3000° C. The hard carbon is a so-called hard black.

In order to improve the thermal transfer efficiency, surface active agents such as glycerine, higher fatty acid non-ionic surface active agents and the like are preferably added. Glycerine ensures good affinity among the respective ingredients and affinity between the cloth or film of the pouch 5 and the ingredients of the fluid. In addition, voids in the fluid which will impede the thermal conductivity can be prevented from being formed. For a good emulsifying property, dispersibility and lubricity, higher fatty acid non-ionic surface active agents are preferably used as the surface active agent. Examples of non-ionic surface active agents include polyethylene glycol and the like.

Likewise, in order to prevent water from becoming foul, sodium chloride and bactericides and/or preservatives may be added. Typical examples of the bactericide and preservative, respectively, include sodium sodium hypochlorite and sodium dehydroacetate. Sodium chloride not only has sterilizing and bactericidal effects, but also is known to have a beneficial to the health even when indirectly contacted to the human body through a thin medium, (e.g. treatment of diabetes).

When the pillow is left alone for 1 hour at a room temperature of 22° C., the user can sleep well comfortably because of gentle cooling of his head. When the pillow was continually used over two hours, the temperature of the pillow was found to be 29° C. (room temperature: 20° C.). Moreover, when the pillow was immersed in water at 10° C., it was cooled down to 12° C. in about three minutes.

In various experimental data, the fluid composition comprises from 35 to 60 wt % of carbon fine particles, from 20 to 50 wt % of water, from 2 to 5 wt % of a surface active agent, from 10 to 30 wt % of sodium chloride, and effective small amounts of a bactericide and a preservative.

If the amount of the fine particles is less than the above range, an intended thermal transfer property may not be attained. A larger amount is not favorable in view of the fluidity of the resulting composition. The reverse is true of the case of water.

Figure 3:
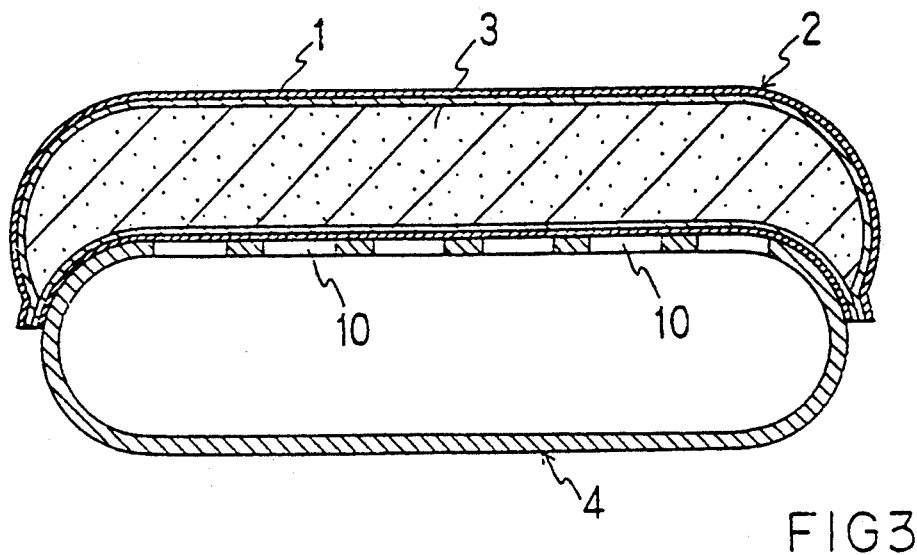
FIG. 3 is a sectional view of a cooling pillow according to a second embodiment of the present invention.

Second Embodiment (FIG. 3)

A cooling pillow according to a second embodiment will be described with reference to FIG. 3.

The pillow comprises a base 4 and a pillow body 2, which is the same as the pillow of the first embodiment and is attached to the base 4 along the heat fused flange 9. The base 4 has a flat cylindrical body which is opened at both ends thereof and has a plurality of holes 10 through which air passes.

With such an arrangement of the pillow, air circulates in the base 4 so that the area of the base 4 to contact air is increased, which enhances the heat exchange with air. The base 4 is formed of a deformable elastic rubber or synthetic rubber so as to facilitate circulation of air when the user shifts sleeping positions. If the deformable elastic rubber or synthetic rubber is mixed with fine particles of hard carbon, the heat exchange with air is further improved.

Figure 4:
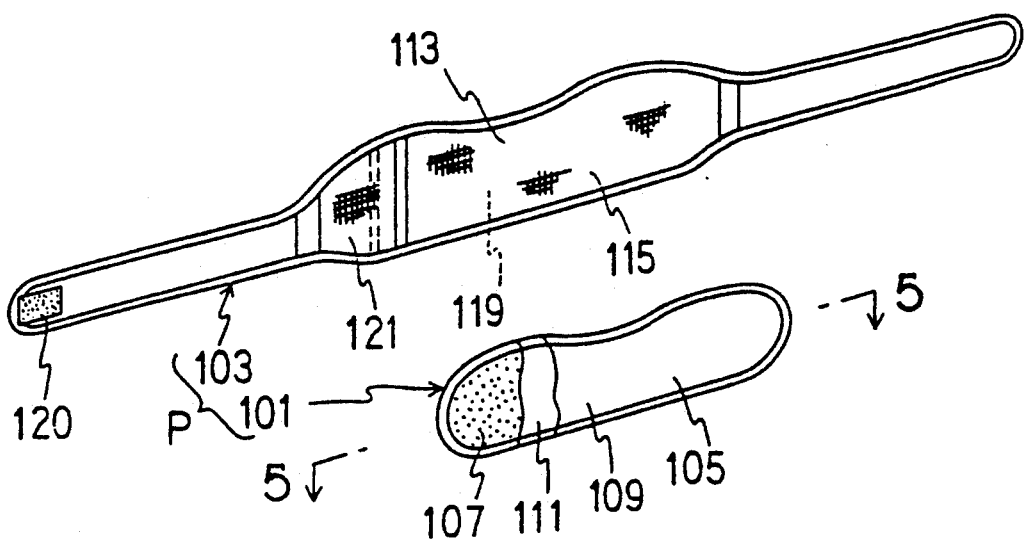
FIG. 4 is a perspective view, partially cut away, of a cooling pad and a pad-holding means, which are not assembled together for illustration, according to a third embodiment of the invention.
Figure 5:
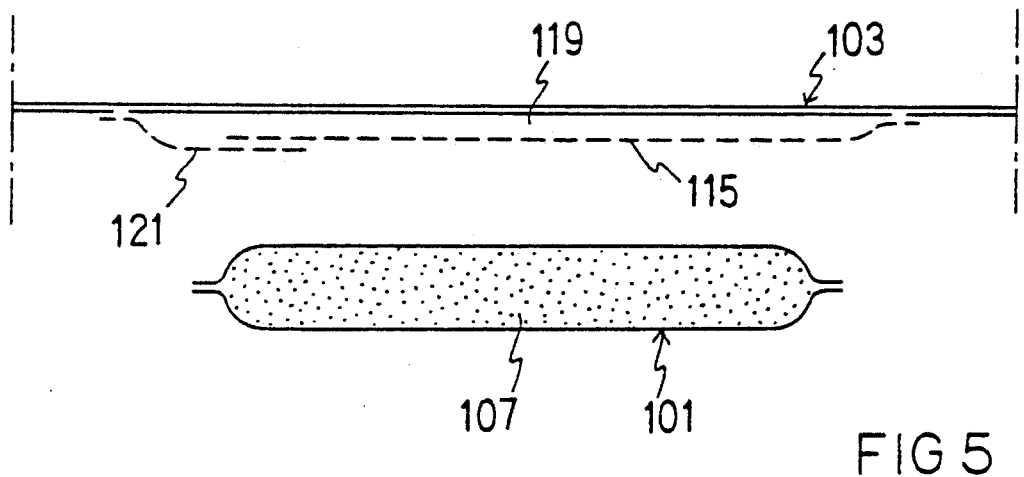
FIG. 5 is an illustrative, enlarged sectional view taken along the line A—A of FIG. 4.
Figure 6:
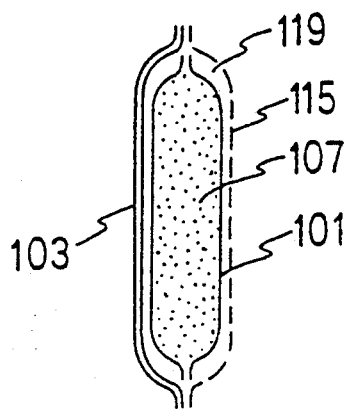
FIG. 6 is an illustrative, enlarged sectional view of a pad in an assembled state.

Third Embodiment (FIGS. 4 to 6)

A cooling device for use in a pad and a pad holding means according to a third embodiment of the present invention will be described with reference to FIGS. 4 to 6.

In these figures, there is shown an eye patch or a forehead patch according to one embodiment of the invention. The patch or cooling device P includes a pad 101 and a bandage 103 for keeping the pad 101 in contact with the eyes or forehead and also for accommodating the pad in position. The bandage 103 is used as a means for keeping the pad 101 in intimate contact with the human body. Depending on the length and/-width of the bandage 103, the patch or holder P may be used to tie it around a leg, arm or trunk.

The pad 101 is in the form of a pouch 105 in which a thermal transfer fluid 107 is hermetically filled. The pouch 105 may be made of a flexible composite film which includes, for example, a laminate of a nylon or polyamide outer film 109 which feels good to the touch and a polyester inner film 111 which has good physical properties. Aside from the laminate film, not only polyvinyl sheets or films, but also other films or sheets may be likewise used.

For the hermetical sealing, the fluid 107 is filled up in the flexible pouch 105, followed by heat sealing under vacuumizing conditions. By this, the phase separation and spoilage of the fluid 107 can be suppressed to a significant extent with an attendant advantage that the thermal transfer rate can be enhanced owing to the degassing.

The thermal transfer fluid 107 should comprise the same fine particles as those of the first embodiment, hence the explanation thereof is omitted.

Broadly, hard carbon includes both graphitic (or fixed) carbon and hard carbon, both of which are known to have very high thermal conductivity. This is considered owing to the existence of free electrons and the thermal conductivity is larger than those of metals. In general, heat passing through a solid matter is transported through carriers (electrons or holes) which take part in electric conduction and also by propagation of lattice vibrations. The thermal conductivity of hard or graphitic carbon is ascribed to the propagation of lattice vibrations which facilitates movement of the carriers.

When the fine particles of hard or graphitic carbon having such a high thermal conductivity as set out above is mixed with water, an aqueous slurry in the form of a gel is obtained. The slurry has high thermal conductivity. If the mixture is filled in a pouch of an eye or forehead patch and allowed to stand at ambient temperatures or immersed in water, the pouch immediately reaches the ambient temperature or the temperature of water.

Where the eye or forehead patch which has been allowed to stand at normal temperatures is used as it is, the normal temperature is usually lower than a bodily temperature (36° C.), i.e. an indoor temperature is usually 25° C. or lower. Accordingly, the heat of eyes or forehead is absorbed through the high thermal conductivity of the fine particles of carbon in the slurry. Thus, the eyes or forehead can be mildly and quickly cooled down to ambient temperatures. The slurry containing the fine particles of carbon absorbs heat from a human body and raises its temperature. However, the fine particles have high thermal conductivity, so that the absorbed heat is efficiently transferred to air or a contacted matter. Thus, the eyes or forehead or body may be continually cooled if the patch is used over a long time.

In addition, hard or graphitic carbon is able to generate far-infrared rays at normal temperatures. The far-infrared rays generated at normal temperatures have a wavelength of 5 to 15 micrometers. The far-infrared rays within the above-indicated range will cause a resonance phenomenon to occur in the body and will have the function of rendering the blood weakly alkaline.

The fluid or slurry 107 is obtained by kneading both fine particles of the carbon and water such as by kneaders or mixers.

In order to cause the pad 1 to intimately contact with human body, there is used the band 103. The band 103 has an eye or forehead covering portion 113 which has, for example, an inner net 115 extending from one side to the other side of the portion 113 while opening at one side end thereof. The inner net 115 is fixed except for the opening (not shown) to the covering portion 113. As a result, a kind of pocket 119 is established between the covering portion 113 and the inner net 115. The pad 101 is accommodated in the pocket 119 as shown in FIG. 6. An outer net 121 is provided as partially superposed over the one end side of the inner net 115 thereby preventing the pad from being removed in a normal condition as is particularly shown in FIG. 5. The band 103 has a velvet-type fastener tape 120 sewed at one inner end side thereof as shown in FIG. 4 so that the band 103 can be fastened, as desired, by contact between the fastener tape 120 and an outer cloth of the band 103.

When used, the pad 1 is placed in the pocket 119. When the band is fastened to be tied around as desired, the pad 101 is contacted with skin through the nets 115 and 121, thereby cooling the body by the action of the fluid composition.

Figure 7:
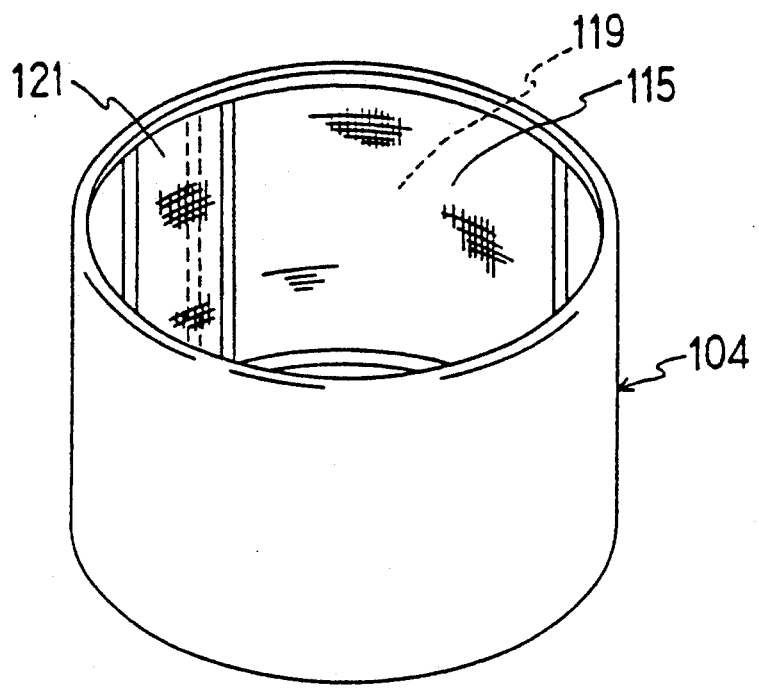
FIG. 7 is a perspective view of a supporter according to a fourth embodiment of the invention.

Fourth Embodiment (FIG. 7)

FIG. 7 shows a fourth embodiment of the invention in which a supporter is illustrated. In the figure, a supporter 104 has an inner net 115 and an outer net 121 at an inner side of the supporter 104. The nets 115 and 121 are so arranged as in FIG. 5, thereby providing a pocket 19 for accommodating the pad 1 shown in the foregoing embodiment. In this case, the supporter 4 serves as a means for intimately contacting the pad 1 to the human body.

Figure 8:
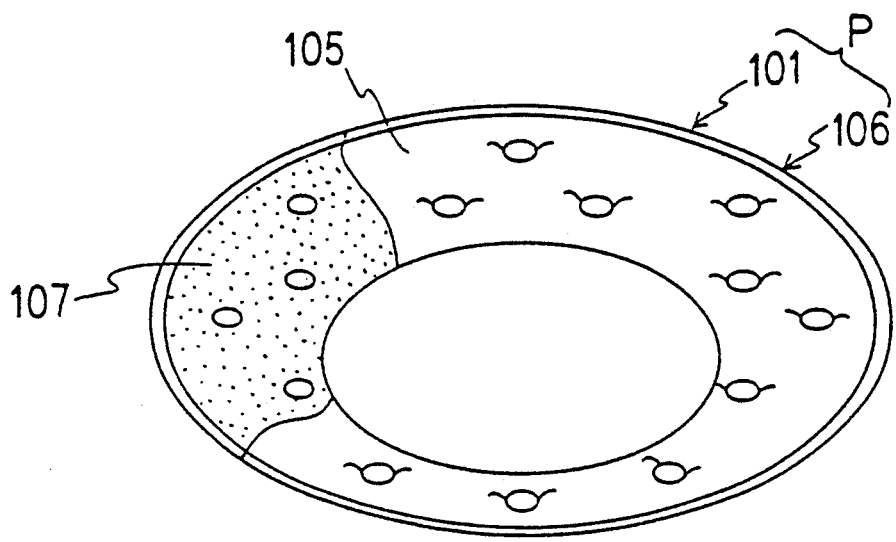
FIG. 8 is a perspective view, partially cut away, of a cooling device according to a fifth embodiment of the invention.

Fifth Embodiment (FIG. 8)

FIG. 8 shows a annular shaped shawl according to a fifth embodiment of the invention. In this embodiment, a cooling pad 101 is shaped substantially in the form of a relatively thin annular shape having an opening at the center thereof, through which head is passed, so that the pad 101 can be snugly placed on the shoulders. In this embodiment, the pad is so shaped and arranged as to constitute the contact means 106. In order that the thermal transfer fluid 107 is uniformly distributed throughout the annular shaped pouch 105, the pouch 105 is intermittently heat sealed as shown in FIG. 8.

The annular shaped shawl as set out above is very effective not only in solving the problem of a stiffness in the shoulders, but also in recovering from fatigues after sports such as swimming or playing of football. Also, the shawl may be effective in relieving one of fatigues when resting in the shade near the sea.

According to the third to fifth embodiments, the slurry was filled up in a pouch of a forehead band P of the type shown in FIGS. 4 to 6 and hermetically sealed to obtain the band. The band was allowed to stand for one hour at an ambient temperature of 22° C. Thereafter, the band was used for cooling the forehead of student panel members. As a result, it was confirmed that the head of the individual members were gently cooled which enhanced efficiency of study.

As will be apparent from the above, the thermal transfer fluid (slurry) which contains fine particles of hard or graphitic carbon having very high thermal conductivity is filled in the pillow and the pad. This is advantageous in that when the pillow and the pad is allowed to stand at normal temperatures, it quickly reaches a temperature close to the normal temperature; that the head and the body can be gently cooled, i.e. when the pillow and the pad is long used, the head and the body is continued to cool to a temperature close to the normal temperature and thus, the use is very simple; and no specific energy is required for cooling.

The use of the cooling material is very convenient in use thereof because of the gentle cooling of the head and body and of the soft contact with the head and body. The cooling material is very adapted for use in the pillow and the pad for mitigating a stiffness in the shoulders and for recovering from fatigue after sports. Furthermore, if the pillow or the pad is cooled by water or in a refrigerator, they are quickly cooled so that they are effective for an unexpected accident or a sudden case of fever, a headache, toothache, hangover, eyestrain, bruise, or sprain.

Still furthermore, the effect of the far-infrared rays caused by hard carbon and graphitic carbon can be used for treating pain and discomfort. The resonance phenomenon caused by the wavelength of the far-infrared rays facilitates not only a safe sleep but also relief to the body and promotion of health.

What is claimed is:

1. A cooling pillow comprising a flexible pouch and a thermal transfer fluid hermetically filling the flexible pouch, said thermal transfer fluid comprising a mixture of fine particles of hard carbon or graphitic carbon and water, the mixing ratio by weight between said fine particles and water being in the range of 75:25 to 60:40.

2. A cooling pillow comprising a flexible pouch and a thermal transfer fluid hermetically filling the flexible pouch, said thermal transfer fluid comprising a mixture of fine particles of hard carbon or graphitic carbon, water, a surface active agent, sodium chloride and effective amounts of a bactericide and a preservative.

3. A cooling pillow according to claim 2, wherein said thermal transfer fluid has a composition which comprises 35 to 60 wt % of fine particles, 20 to 50 wt % of water, 2 to 5 wt % of the surface active agent, 10 to 30 wt % of sodium chloride, and small effective amounts of the bactericide and the preservative, the total being 100 wt %.

4. A cooling pillow according to claim 3, wherein said surface active agent is glycerine.

5. A cooling pillow according to claim 3, wherein said surface active agent is a higher fatty acid non-ionic surface active agent.

6. A cooling device comprising a pad having a flexible pouch and a thermal transfer fluid hermetically filling the flexible pouch, and pad holding means for holding the pad in contact with the human body, said thermal transfer fluid comprising a mixture of fine particles of hard carbon or graphitic carbon and water, the mixing ration by weight between said fine particles and water being in the range of 75:25 to 60:40.

7. A cooling device comprising a pad having a flexible pouch and a thermal transfer fluid hermetically filling the flexible pouch, and pad holding means for holding the pad in contact with the human body, said thermal transfer fluid comprising a mixture of fine particles of hard carbon or graphitic carbon, water, a surface active agent, sodium chloride, and effective amounts of a bactericide and a preservative.

8. A cooling device according to claim 7, wherein said thermal transfer fluid has a composition which comprises 35 to 60 wt % of the fine particles, 20 to 50 wt % of water, 2 to 5 wt % of the surface active agent, 10 to 30 wt % of sodium chloride, and small effective amounts of the bactericide and the preservative, the total being 100 wt %.

9. A cooling device according to claim 8, wherein said surface active agent is glycerine.

10. A cooling device according to claim 8, wherein said surface active agent is a higher fatty acid non-ionic surface active agent.

* * * * *

UNITED STATES PATENT AND TRADEMARK OFFICE
CERTIFICATE OF CORRECTION

PATENT NO. : 5,274,865
DATED : January 4, 1994
INVENTOR(S) : Takeshige TAKEHASHI It is certified that error appears in the above-identified patent and that said Letters Patent is hereby corrected as shown below:

Column 8, line 7; change "ration" to ---ratio---.

Signed and Sealed this

Fourteenth Day of June, 1994

Attest:

BRUCE LEHMAN

Attesting Officer     Commissioner of Patents and Trademarks